(12) United States Patent
Hochmair

(10) Patent No.: US 7,609,061 B2  
(45) Date of Patent: Oct. 27, 2009

(54) DEMAGNETIZED IMPLANT FOR MAGNETIC RESONANCE IMAGING

(75) Inventor: Ingeborg Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 12/171,441

(22) Filed: Jul. 11, 2008

(65) Prior Publication Data

US 2009/0015255 A1 Jan. 15, 2009

Related U.S. Application Data

(60) Provisional application No. 60/949,560, filed on Jul. 13, 2007.

(51) Int. Cl.  
*G01V 3/00* (2006.01)

(52) U.S. Cl. ........................ 324/307; 600/409

(58) Field of Classification Search .............. 324/307, 324/309; 600/409  
See application file for complete search history.

(56) References Cited

U.S. PATENT DOCUMENTS

| | | | |
|---|---|---|---|
| 3,487,403 A | 12/1969 | Pihl | 340/373 |
| 3,573,812 A | 4/1971 | Pihl | 340/373 |
| 3,801,767 A | 4/1974 | Marks | 200/161 |
| 3,987,967 A | 10/1976 | Kuznetsov et al. | 241/1 |
| 4,038,990 A | 8/1977 | Thompson | 128/419 PG |
| 4,199,741 A | 4/1980 | Paulet | 335/206 |
| 4,257,936 A | 3/1981 | Matsumoto et al. | 524/413 |
| 4,317,969 A | 3/1982 | Riegler et al. | 200/52 R |
| 4,596,971 A | 6/1986 | Hirabayashi et al. | 335/205 |
| 4,628,907 A | 12/1986 | Epley | 128/1.6 |
| 4,785,816 A | 11/1988 | Dow et al. | 600/446 |
| RE32,947 E | 6/1989 | Dormer et al. | 128/420.6 |
| 4,868,530 A | 9/1989 | Ahs | 335/207 |
| 4,918,745 A | 4/1990 | Hutchinson | 455/41 |
| 5,015,224 A | 5/1991 | Maniglia | 600/25 |
| 5,183,056 A | 2/1993 | Dalen et al. | 600/595 |
| 5,434,549 A | 7/1995 | Hirabayashi et al. | 335/229 |
| 5,456,654 A | 10/1995 | Ball | 600/25 |
| 5,494,035 A * | 2/1996 | Leuthold et al. | 600/409 |
| 5,538,219 A | 7/1996 | Osterbrink | 251/129.15 |

(Continued)

FOREIGN PATENT DOCUMENTS

SU 1690749 11/1991

(Continued)

OTHER PUBLICATIONS

Hobbs, et al, "Magnetic Resonance Image—Guided Proteomics of Human Glioblastoma Multiforme", *Journal of Magnetic Resonance Imaging*, pp. 530-536 (2003).

(Continued)

*Primary Examiner*—Louis M Arana  
(74) *Attorney, Agent, or Firm*—Sunstein Kann Murphy & Timbers LLP

(57) ABSTRACT

A method of operating a magnetic resonance imaging (MRI) system is described. A magnetic element in an implanted medical device is demagnetized by exposing it to an external demagnetizing magnetic field. Magnetic resonance imaging of the patient is performed. Then the magnetic element is remagnetized without removing it from the implanted medical device by exposing the magnetic element to an external remagnetizing magnetic field.

6 Claims, 5 Drawing Sheets

U.S. PATENT DOCUMENTS

| | | | |
|---|---|---|---|
| 5,630,835 A | 5/1997 | Brownlee | 607/60 |
| 5,716,407 A | 2/1998 | Knapp et al. | 623/11 |
| 5,724,014 A | 3/1998 | Leikus et al. | 335/4 |
| 5,749,912 A | 5/1998 | Zhang et al. | 607/57 |
| 5,857,958 A | 1/1999 | Ball et al. | 600/25 |
| 5,877,664 A | 3/1999 | Jackson, Jr. | 335/205 |
| 6,040,762 A | 3/2000 | Tompkins | 340/426 |
| 6,175,767 B1 | 1/2001 | Doyle, Sr. | 607/57 |
| 6,178,079 B1 | 1/2001 | Renger | 361/118 |
| 6,178,353 B1 | 1/2001 | Griffith et al. | 607/61 |
| 6,190,305 B1 | 2/2001 | Ball et al. | 600/25 |
| 6,208,235 B1 | 3/2001 | Trontelj | 340/10.1 |
| 6,217,508 B1 | 4/2001 | Ball et al. | 600/25 |
| 6,219,580 B1 | 4/2001 | Faltys et al. | 607/57 |
| 6,292,678 B1 | 9/2001 | Hall et al. | 600/374 |
| 6,295,472 B1 | 9/2001 | Rubinstein et al. | 607/55 |
| 6,313,551 B1 | 11/2001 | Hazelton | 310/12 |
| 6,348,070 B1 * | 2/2002 | Teissl et al. | 623/11.11 |
| 6,358,281 B1 | 3/2002 | Berrang et al. | 623/10 |
| 6,505,062 B1 | 1/2003 | Ritter et al. | 600/407 |
| 6,506,987 B1 | 1/2003 | Woods | 290/61.62 |
| 6,522,909 B1 | 2/2003 | Garibaldi et al. | 600/424 |
| 2002/0133225 A1 * | 9/2002 | Gordon | 623/1.42 |
| 2006/0244560 A1 | 11/2006 | Zimmerling et al. | 355/207 |
| 2008/0021518 A1 | 1/2008 | Hochmair et al. | 607/57 |

FOREIGN PATENT DOCUMENTS

| | | |
|---|---|---|
| WO | WO 97/32629 | 9/1997 |
| WO | WO 03/081976 | 10/2003 |
| WO | WO 03/092326 | 11/2003 |
| WO | WO 2004/114723 | 12/2004 |

OTHER PUBLICATIONS

Risi, F. et al., "Magnetic Resonance Imaging Safety of Nucleus® 24 Cochlear Implants at 3.0 T," Int'l Congress Series, Excerpta Medica, Amsterdam, vol. 1273, Nov. 1, 2004.

Heller, et al, "Evaluation of MRI Compatibility of the Modified Nucleus Multichannel Auditory Brainstem and Cochlear Implants", *The American J. Of Otology* 17(5): pp. 724-729., Sep. 1996.

Teissl, et al, "Cochlear Implants: In vitro Investigation of Electromagnetic Interference at MR Imaging—Compatibility and Safety Aspects", *Radiology* 208(3); pp. 700-708; Sep. 1998.

Teissl, et al, "Magnetic Resonance Imaging and Cochlear Implants: Compatibility and Safety Aspects", *J. Magn. Reson. Imaging*, 9(1); pp. 26-38; Jan. 1999.

International Searching Authority, International Search Report dated Nov. 21, 2008, International application No. PCT/US2008/069738.

* cited by examiner

DEMAGNETIZED IMPLANT FOR MAGNETIC RESONANCE IMAGING

This application claims priority from U.S. Provisional Patent Application 60/949,560, filed Jul. 13, 2007, which is hereby incorporated by reference.

FIELD OF THE INVENTION

The present invention relates to implantable medical devices, and specifically, to demagnetization and remagnetization of magnetic elements in such devices to allow for magnetic resonance imaging.

BACKGROUND ART

Some implantable medical devices use magnets to hold internal and external pieces in proper position. For example, as shown in FIG. 1, an idealized cochlear implant system may include a receiving coil 108 located under the skin 103 and embedded in or just on top of the bone 104. An implanted internal magnet 106 is contained in the center of the receiving coil 108. An external transmitter housing 101 includes an external magnet 105 that is positioned over the internal magnet 106 so that the external transmitter housing 101 is held in place in an optimum position adjacent to the receiving coil assembly 102. When such an optimal position is maintained, an external transmitting coil 107 within the transmitter housing 101 can use inductive coupling to transmit a transcutaneous data and/or power signal to the receiving coil 108.

The receiving coil 108 may, for example, be encapsulated within some tissue-compatible organic material such as silicone or epoxy, forming a receiving coil assembly 102. In such an arrangement, the receiver coil assembly 102 is connected to receiver electronic circuits within a metal or ceramic case which is hermetically sealed from the surrounding tissue. Or, in another approach, the internal magnet 106, receiving coil 108 and the receiver electronic circuits are all contained within a common hermetic case. In any such arrangement, the internal magnet 106 is a permanently integrated part of the implant structure.

One problem arises when the patient undergoes Magnetic Resonance Imaging (MRI) examination. Interactions occur between the receiver magnet and the applied external magnetic field for the MRI. As shown in FIG. 2, the external magnetic field $\vec{B}$ from the MRI may create a torque $\vec{T}$ on an implanted internal magnet 202, which may displace the internal magnet 202 or the whole coil assembly 201 out of proper position. Among other things, this may damage the adjacent tissue in the patient. In addition, the external magnetic field $\vec{B}$ from the MRI may reduce or remove the magnetization $\vec{m}$ of the internal magnet 202. As a result, the demagnetized internal magnet 202 may no longer be strong enough after exposure to the external magnetic field $\vec{B}$ of the MRI to hold the external transmitter housing in proper position. The implanted internal magnet 202 may also cause imaging artifacts in the MRI image, there may be induced voltages in the receiving coil, and hearing artifacts due to the interaction of the external magnetic field $\vec{B}$ of the MRI with the implanted device.

Therefore, implants with removable magnets have been developed. FIG. 3 shows a portion of a typical implant system using magnets according to one approach used in the prior art. An external transmitter housing 301 includes transmitting coils 302 and an external magnet 303. The external magnet 303 has a conventional coin-shape and north and south magnetic poles as shown which produce external magnetic field lines 304. Implanted under the patient's skin is a corresponding receiver assembly 305 having similar receiving coils 306 and an implanted internal magnet 307. The internal magnet 307 also has a coin-shape and north and south magnetic poles as shown which produce internal magnetic field lines 308. The internal receiver housing 305 is surgically implanted and fixed in place within the patient's body. The external transmitter housing 301 is placed in proper position over the skin covering the internal receiver assembly 305 and held in place by interaction between the internal magnetic field lines 308 and the external magnetic field lines 304. Rf signals from the transmitter coils 302 couple data and/or power to the receiving coil 306 which is in communication with an implanted processor module (not shown).

The arrangement in FIG. 3 differs from the earlier prior art in that the implant is designed so that the internal magnet 307 is removable by a first pre-MRI surgery. This eliminates the problems of torque, demagnetization, and image artifacts caused by the magnet during the MRI procedure. Then, after the MRI, a second post-MRI surgery is necessary to replace the internal magnetic 307. While this arrangement allows implant users to receive MRI's when necessary, the requirement for two surgeries raises issues and problems of its own.

SUMMARY OF THE INVENTION

Embodiments of the present invention are directed to a method of operating a magnetic resonance imaging (MRI) system. A magnetic element in an implanted medical device is demagnetized by exposing it to an external demagnetizing magnetic field. Magnetic resonance imaging of the patient is performed. Then the magnetic element is remagnetized without removing it from the implanted medical device by exposing the magnetic element to an external remagnetizing magnetic field.

In various specific embodiments, the magnetic resonance imaging may be performed after or while generating the demagnetizing magnetic field. The MRI system may be a high field MRI system, for example, a 3T or 6T MRI system. In some embodiments, the implanted medical device may be a cochlear implant system.

Embodiments of the present invention also include an implanted medical device processed by any of the above methods.

DETAILED DESCRIPTION OF SPECIFIC EMBODIMENTS

Embodiments of the present invention are directed to techniques for magnetic resonance imaging which reduce the torque exerted on magnet elements of implanted medical devices, reduce MRI imaging artifacts produced by magnetic field distortions related to the implanted magnetic elements, and also reduce linear force created on such implanted magnetic elements. This is accomplished without first removing the magnet element (or any other part of the implanted medical device) before the MRI scan is performed.

Figure 1:
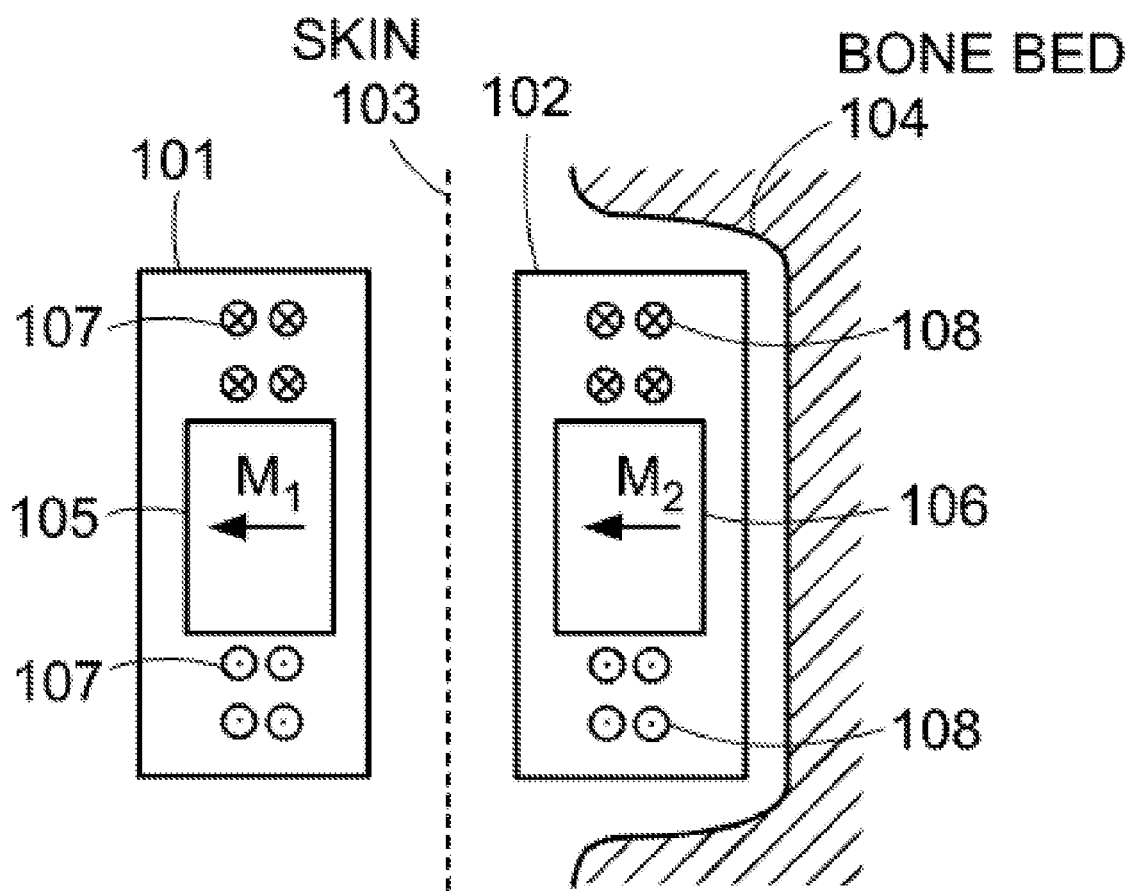
FIG. 1 shows a portion of a typical idealized cochlear implant which may be used in embodiments of the present invention.
Figure 2:
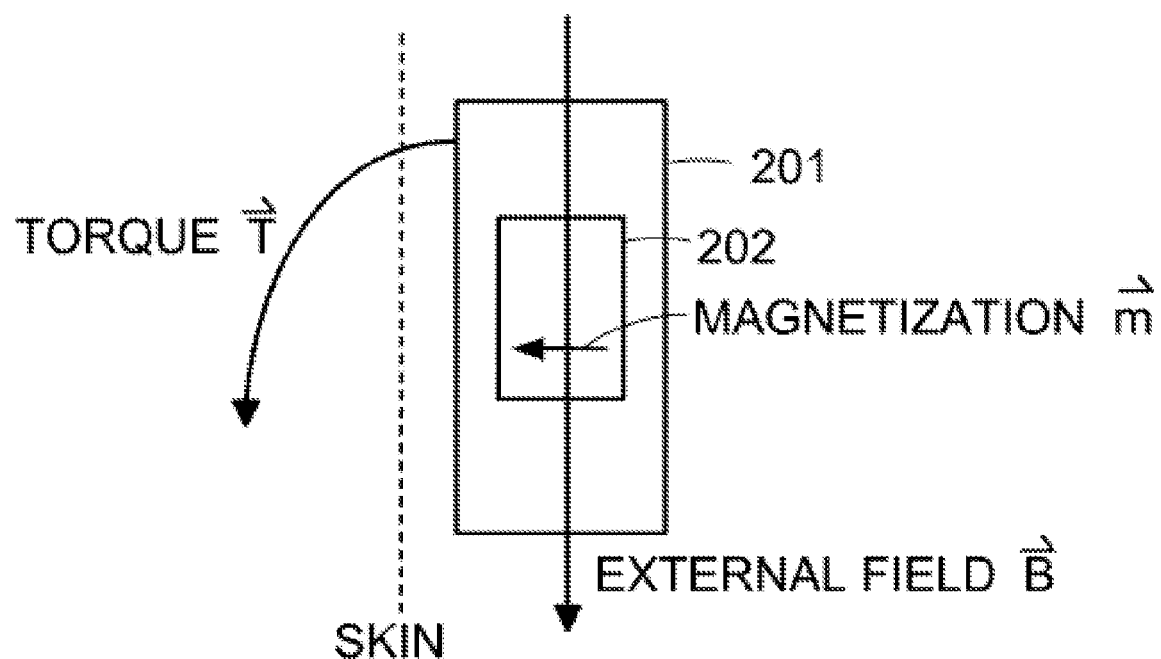
FIG. 2 shows effects of an external magnetic field on an implanted portion of an implanted device which may be used in embodiments of the present invention.
Figure 3:
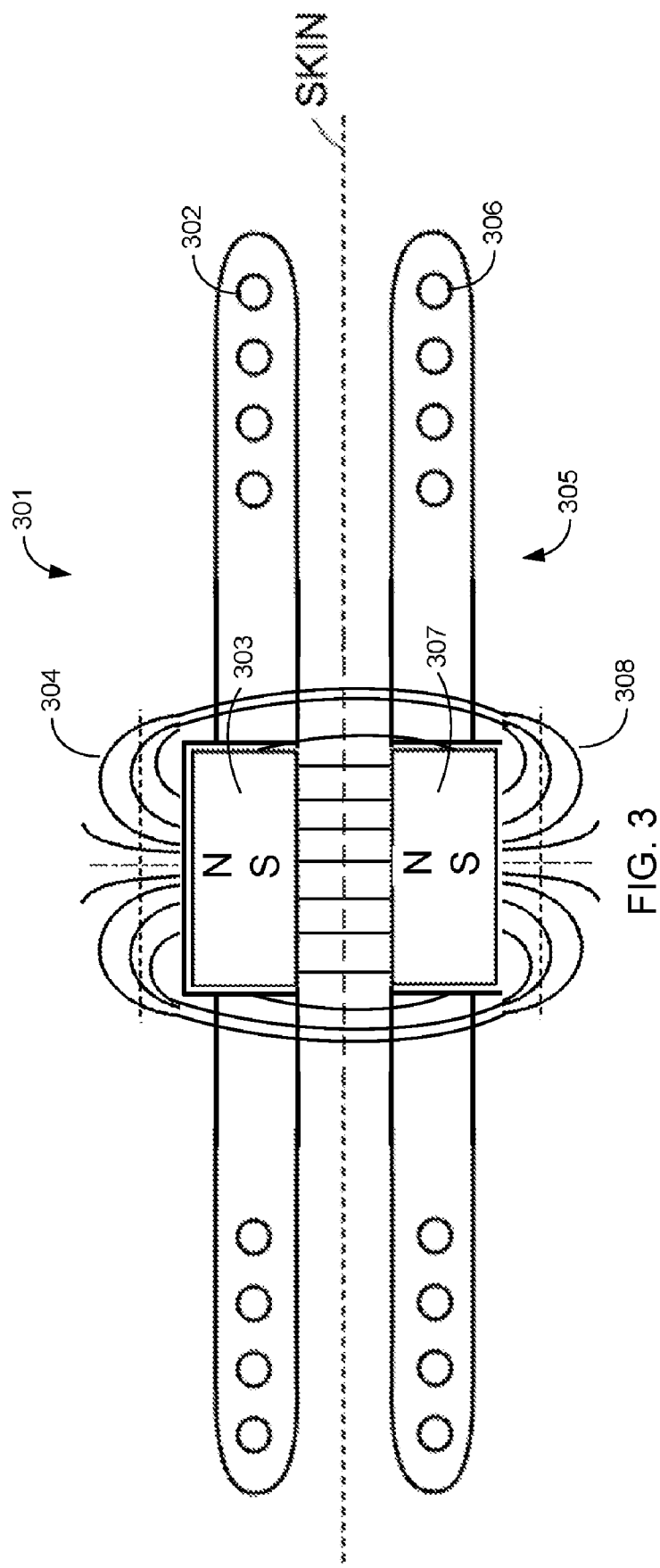
FIG. 3 shows a portion of a typical implant system using magnets according to embodiments of the present invention.
Figure 4:
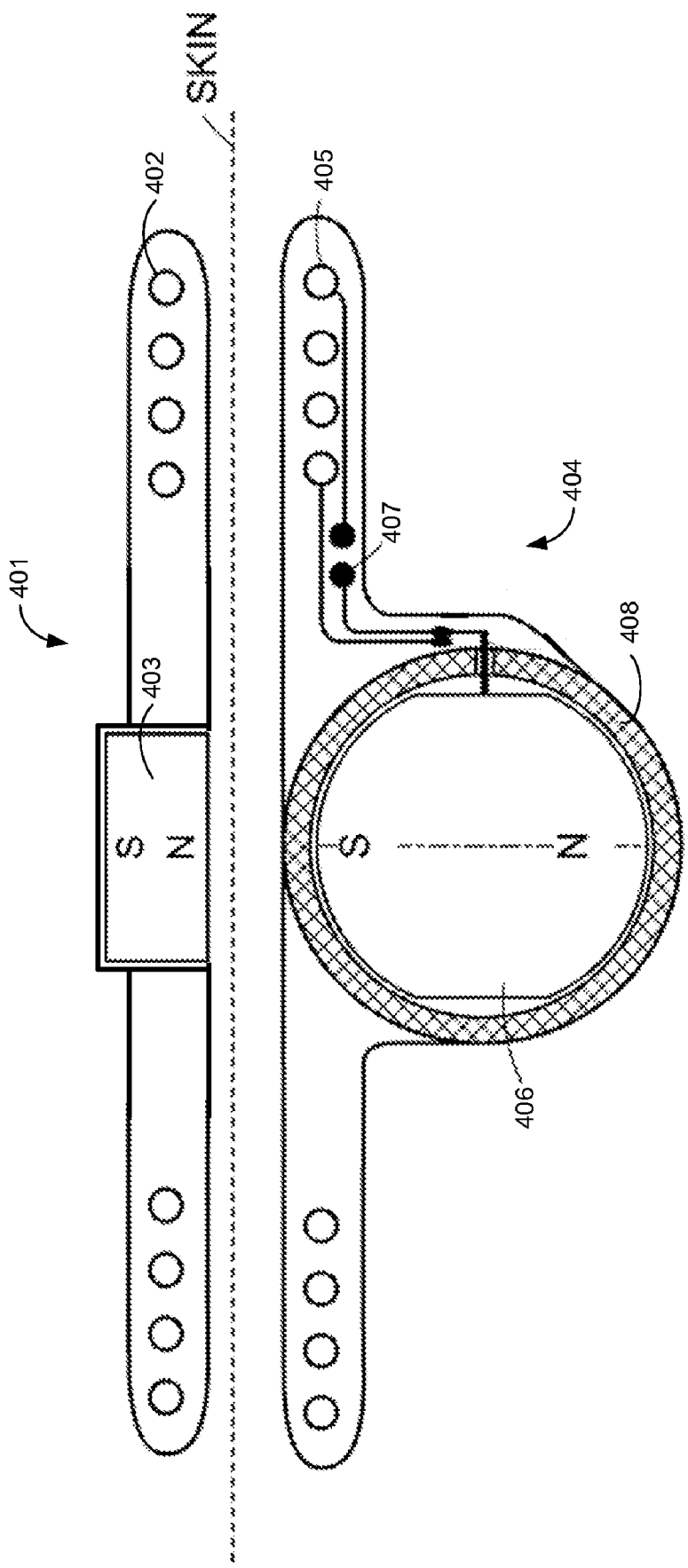
FIG. 4 shows a portion of a typical implant system using a low-torque magnet according to embodiments of the present invention.

Some MRI related problems recently have been addressed by using an implanted magnet structured to avoid producing torque in an MRI field. One example of such an arrangement is shown in FIG. 4, which is based on the disclosure of U.S. Patent Publication 20060244560, the contents of which are incorporated herein by reference. The external transmitter housing 401 is basically the same as in FIG. 3, with transmitting coils 402 and an external magnet 403. The implanted receiver assembly 404 has corresponding receiving coils 405 and an implanted internal magnet 406, as well as connecting wiring 407 to a separate processor module. But in FIG. 4, the internal magnet 406 has a cylindrical or spherical shape. A ball-shaped welded case 408 (e.g., of titanium or niobium) hermetically encapsulates and isolates the internal magnet 406 from the body tissues (otherwise, it might rapidly corrode). As a result, the internal magnet 406 is able to rotate to re-align itself to an external MRI magnetic field without producing a torque, becoming demagnetized, or creating induced voltages, etc. This avoids many of the problems of the earlier arrangement shown in FIG. 3. Typically, a patient having an implant as shown in FIG. 4 may undergo MRI without surgeries to remove and replace the internal magnet 406. But even in this arrangement, there may still be imaging artifacts due to the internal magnet 406, especially in the nearby region adjacent to the magnet.

Embodiments of the present invention may be used in conjunction with an implanted medical device such as the structures shown in FIGS. 1-4 while avoiding some of the problems described above. With reference for example to FIG. 4, a magnetic element in an implanted medical device, such the internal magnet 406 in the implanted receiver assembly 404, is demagnetized by exposing it to an external demagnetizing magnetic field. Magnetic resonance imaging of the patient is performed. Then the magnetic element is remagnetized without removing it from the implanted medical device by exposing the magnetic element to an external remagnetizing magnetic field.

Figure 5:
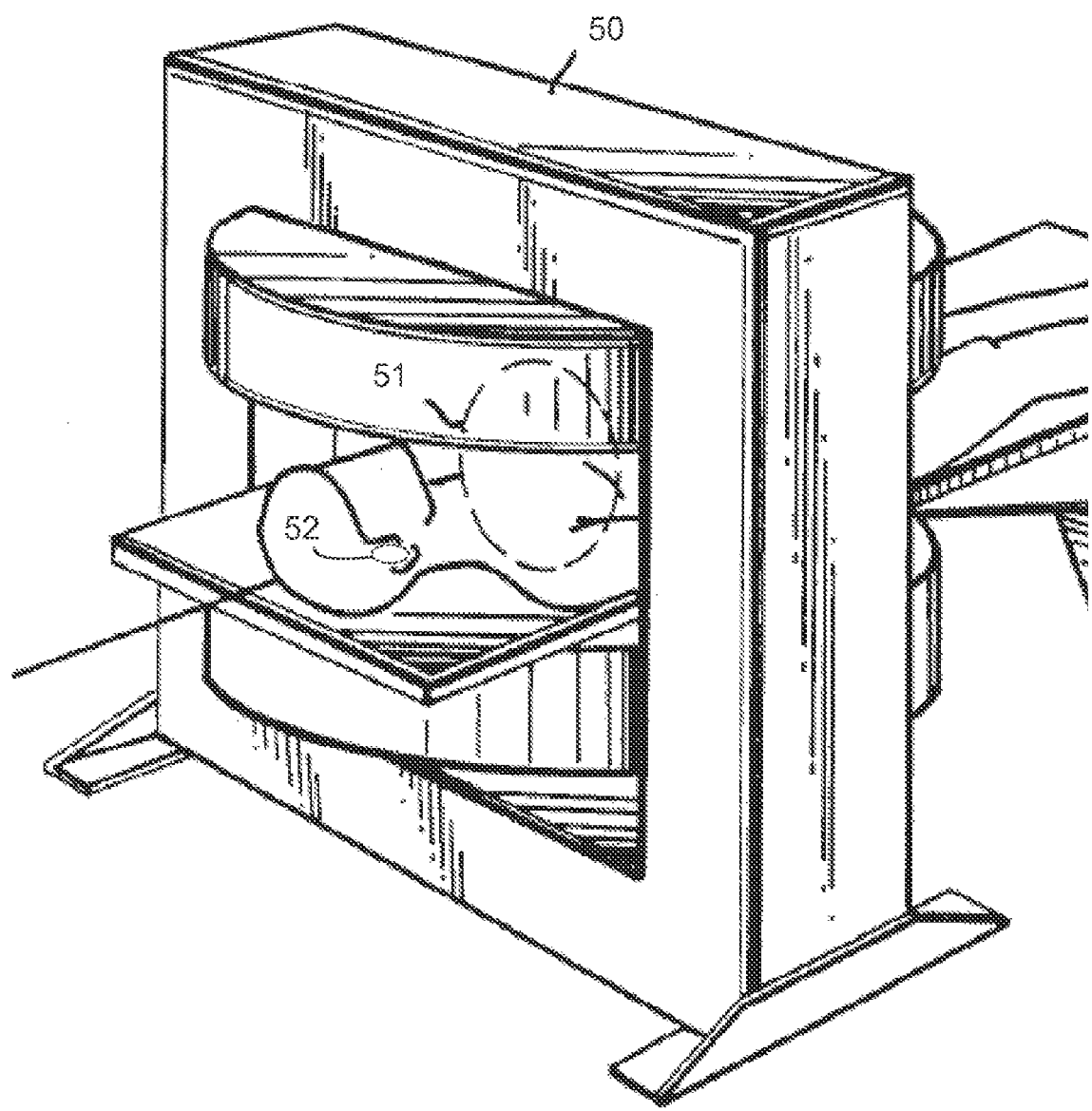
FIG. 5 shows an example of an implantable medical device and an MRI system suitable for use with a method according to an embodiment of the present invention.

Depending on various factors, the magnetic element may be demagnetized either before or while performing the magnetic resonance imaging. As shown in FIG. 5, before the MRI scan, the magnetic element 52 in an implanted medical device may be demagnetized by the magnetic field 51 of the MRI scanner 50. For example, it has been demonstrated with a 6T-MRI scanner that pre-scan demagnetization can be accomplished by correctly orienting the head of the patient in front of the bore of the scanner 50 and applying the magnetic field 51. Then, the patient's head can be reoriented as desired for correct MRI imaging and the patient may full enter the bore of the scanner 50 for normal MRI imaging. Post-imaging, remagnetization of the magnetic element 52 can be performed by correctly re-orienting the head of the patient in front of the bore of the scanner 50 and reapplying the magnetic field 51.

In an alternative embodiment, if the imaging artifacts are of lesser concern, the demagnetization of the magnetic element 52 can be allowed to occur during the normal MRI scanning, and only the remagnetization part of the procedure might be needed. For example, this could be applied as a standard procedure with 3T MRI-scanners which will be used more and more in the future. If reducing imaging artifacts is of greater importance, e.g., in neurofibromatosis II patients where one is concerned with tumor regrowth after surgical removal (especially in the vicinity of the magnetic element such as a cochlear implant structure), the demagnetization may be preferred to be more pronounced, and so a demagnetization process may use a high field MRI-machine (e.g., 6T or higher) before the actual imaging scan, and, of course, a remagnetization process afterwards.

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of operating a magnetic resonance imaging (MRI) system, the method comprising:
   a. demagnetizing a magnetic element in an implanted medical device by exposing it to an external demagnetizing magnetic field;
   b. performing magnetic resonance imaging of the patient while or after exposing the magnetic element to the demagnetizing field; and
   c. remagnetizing the magnetic element without removing it from the implanted medical device by exposing the magnetic element to an external remagnetizing magnetic field.

2. A method according to claim 1, wherein the MRI system is a high field MRI system.

3. A method according to claim 2, wherein the high field MRI system is at least a 3T MRI system.

4. A method according to claim 2, wherein the high field MRI system is at least a 6T MRI system.

5. A method according to claim 1, wherein the implanted medical device is a cochlear implant system.

6. An implanted medical device processed by a method according to any of claims 1 or 2-5.

* * * * *